(12) United States Patent
Laayoun et al.

(10) Patent No.: US 6,489,114 B2
(45) Date of Patent: Dec. 3, 2002

(54) PROCESS FOR LABELING A RIBONUCLEIC ACID, AND LABELED RNA FRAGMENTS WHICH ARE OBTAINED THEREBY

(75) Inventors: Ali Laayoun, Lyons (FR); Duc Do, San Jose, CA (US); Charles G. Miyada, San Jose, CA (US)

(73) Assignees: BIO Merieux, Marcy l'Etoile (FR); Affymetrix, Inc., Santa Clara, CA (US)

(*) Notice: Subject to any disclaimer, the term of this patent is extended or adjusted under 35 U.S.C. 154(b) by 112 days.

(21) Appl. No.: 09/737,761

(22) Filed: Dec. 18, 2000

(65) Prior Publication Data

US 2001/0044105 A1 Nov. 22, 2001

Related U.S. Application Data

(60) Provisional application No. 60/172,135, filed on Dec. 17, 1999.

(51) Int. Cl.$^7$ ............................ C12Q 1/68; C12P 19/34; C12N 7/00; C07H 21/04; C07D 225/00
(52) U.S. Cl. ..................... 435/6; 435/91.1; 435/91.2; 435/91.51; 435/235.1; 435/375; 536/24.2; 540/465; 540/474; 935/29; 935/39; 935/73
(58) Field of Search .................. 435/6, 91.51, 235.1, 435/91.1, 91.2, 375; 540/465, 474; 536/24.2; 935/29, 39, 73

(56) References Cited

U.S. PATENT DOCUMENTS

| | | | |
|---|---|---|---|
| 4,683,195 A | | 7/1987 | Mullis et al. |
| 4,683,202 A | | 7/1987 | Mullis |
| 4,786,600 A | | 11/1988 | Kramer et al. |
| 4,800,159 A | | 1/1989 | Mullis et al. |
| 4,868,105 A | | 9/1989 | Urdea et al. |
| 5,124,246 A | | 6/1992 | Urdea et al. |
| 5,130,238 A | | 7/1992 | Malek et al. |
| 5,171,853 A | | 12/1992 | Thorp et al. |
| 5,202,231 A | | 4/1993 | Drmanac et al. |
| 5,317,098 A | | 5/1994 | Shizuya et al. |
| 5,328,824 A | | 7/1994 | Ward et al. |
| 5,399,491 A | | 3/1995 | Kacian et al. |
| 5,407,797 A | | 4/1995 | Marliere et al. |
| 5,422,252 A | | 6/1995 | Walker et al. |
| 5,437,990 A | | 8/1995 | Burg et al. |
| 5,445,934 A | | 8/1995 | Fodor et al. |
| 5,449,767 A | | 9/1995 | Ward et al. |
| 5,501,953 A | * | 3/1996 | Fujita et al. .................. 435/6 |
| 5,525,464 A | | 6/1996 | Drmanac et al. |
| 5,554,516 A | | 9/1996 | Kacian et al. |
| 5,582,829 A | * | 12/1996 | Alliger et al. ............ 424/234.1 |
| 5,585,481 A | | 12/1996 | Arnold, Jr. et al. |
| 5,605,796 A | | 2/1997 | Chen et al. |
| 5,684,149 A | * | 11/1997 | Morrow ...................... 540/474 |
| 5,688,670 A | * | 11/1997 | Szostak et al. ........... 435/91.21 |
| 5,700,637 A | | 12/1997 | Southern |
| 5,744,305 A | | 4/1998 | Fodor et al. |
| 5,766,849 A | | 6/1998 | McDonough et al. |
| 5,807,522 A | | 9/1998 | Brown et al. |
| 5,871,976 A | * | 2/1999 | Kramer et al. ............ 435/91.51 |
| 5,981,734 A | | 11/1999 | Mirzabekov et al. |
| 5,989,904 A | | 11/1999 | Das et al. |

FOREIGN PATENT DOCUMENTS

| | | |
|---|---|---|
| DE | A 3 910 151 | 10/1990 |
| DE | 198 15 864 A1 | 10/1999 |
| EP | A 0 063 879 | 11/1982 |
| EP | 0 097 373 | 1/1984 |
| EP | A 0 280 058 | 8/1988 |
| EP | A 0 286 898 | 10/1988 |
| EP | A 0 302 175 | 2/1989 |
| EP | A 0 320 308 | 6/1989 |
| EP | A 0 329 198 | 8/1989 |
| EP | A 0 567 841 | 11/1993 |
| EP | A 0 709 468 | 5/1996 |
| EP | 0 801 072 A | 10/1997 |
| FR | 2 768 743 | 3/1999 |
| FR | 2 781 500 | 1/2000 |
| WO | WO A 88/01302 | 2/1988 |
| WO | WO A 88/04300 | 6/1988 |
| WO | WO A 88/10315 | 12/1988 |
| WO | WO A 90/14439 | 11/1990 |
| WO | WO A 93/16094 | 8/1993 |
| WO | WO 93/20241 | 10/1993 |
| WO | WO A 93/22461 | 11/1993 |
| WO | WO A 94/03472 | 2/1994 |
| WO | WO A 94/29723 | 12/1994 |
| WO | WO A 95/03142 | 2/1995 |
| WO | WO A 95/03430 | 2/1995 |
| WO | WO A 95/08000 | 3/1995 |
| WO | WO A 95/11995 | 5/1995 |
| WO | WO A 96/19729 | 6/1996 |
| WO | WO A 96/28460 | 9/1996 |
| WO | WO A 98/05766 | 2/1998 |
| WO | WO A 98/11104 | 3/1998 |
| WO | WO 98/27229 | 6/1998 |
| WO | WO 99/65926 | 12/1999 |

OTHER PUBLICATIONS

Chee, M. et al., "Accessing Genetic Information with High–Density DNA Arrays," Science, vol. 274, pp. 610–614, 1996.
Caviani Pease, A. et al., "Light–generated oligonucleotide arrays for rapid DNA sequence analysis," Proc. Natl. Acad. Sci. USA, vol. 91, pp. 5022–5026, 1994.
Sambrook, J. et al., "Molecular Cloning, a Laboratory Manual," Cold Spring Harbor Laboratory Press, Second Edition, pp. 5.30–5.95, 1989.

(List continued on next page.)

Primary Examiner—W. Gary Jones
Assistant Examiner—Arun Chakrabarti
(74) Attorney, Agent, or Firm—Oliff & Berridge, PLC

(57) ABSTRACT

A process is provided for labeling with signal amplification a ribonucleic acid (RNA), comprising fragmenting the RNA to form RNA fragments, fixing a first ligand to a terminal phosphate located at least one of the 3' end and the 5' end of each of a plurality of the RNA fragments, the terminal phosphate having been released during the fragmentation, and binding a plurality of labeling agents to the first ligand on each of a plurality of the fragments.

25 Claims, 1 Drawing Sheet

OTHER PUBLICATIONS

Lindahl, T. et al., "Rate of Chain Breakage at Apurinic Sites in Double–Stranded Deoxyribonucleic Acid," Biochemistry, vol. 11, No. 19, pp. 3618–3623, 1972. and binding a plurality of labeling agents to the first ligand on each of a plurality of the fragments.

Liuzzi, M. et al., "Characterization of damage in γ–irradiated and $OsO_4$–treated DNA using methoxyamine," Int. J. Radiat. Biol., vol. 54, No. 5, pp. 709–722, 1988.

Breslow, R. et al., "Recognition and catalysis in nucleic acid chemistry," Proc. Natl. Acad. Sci. USA, vol. 90, pp. 1201–1207, 1993.

Hovinen, J. et al., "Imidazole Tethered Oligodeoxyribonucleotides: Synthesis and RNA Cleaving Activity," J. Org. Chem., vol. 60, pp. 2205–2209, 1995.

Blattner, F. et al., "The Complete Genome Sequence of *Escherichia coli* K–12," Science, vol. 277, pp. 1453–1462, 1997.

Abravaya, K. et al., "Strategies to Avoid Amplicon Contamination," Nucleic Acid Amplification Technologies, pp. 125–133, 1997.

Chevalier, J. et al., "Biotin and Digoxigenin as Labels for Light and Electron Microscopy in Situ Hybridization Probes: Where Do We Stand?" J. Histochem. Cytochem., vol. 45, No. 4, pp. 481–491, 1997.

Greisen, K. et al., "PCR Primers and Probes for the 16S rRNA Gene of Most Species of Pathogenic Bacteria, Including Bacteria Found in Cerebrospinal Fluid," J. Clinical Microbiol., vol. 32, No. 2, pp. 335–351, 1994.

Troesch, A. et al., "Mycobacterium Species Identification and Rifampin Resistance Testing with High–Density DNA Probe Arrays," J. Clinical Microbiol., vol. 37, No. 1, pp. 49–55, 1999.

Furuta, T. et al., "Direct Esterification of Phosphates with Various Halides and its Application to Synthesis of cAMP Alkyl Triesters," J. Chem. Soc. Perkin Trans., vol. 1, pp. 3139–3142, 1993.

Sambrook, J. et al., "Removal of Ethidium Bromide from DNAs Purified by Equilibrium Centrifugation in CaCl–Ethidium Bromide Gradients," Plasmid Vectors, $2^{nd}$ Edition, p. 1.46, 1989.

AmpliScribe™ T7, T3, and SP6 High Yield Transcription Kits Product Information, Epicentre Technologies, pp. 1–3, Date Unknown.

Zuckermann, R. et al., "Site–selective cleavage of structured RNA by a staphylococcal nuclease–DNA hybrid," Proc. Natl. Acad. Sci. USA, vol. 86, pp. 1766–1770, 1989.

Gish, G. et al., "DNA and RNA Sequence Determination Based on Phosphorothioate Chemistry," Science, vol. 240, pp. 1520–1522, 1988.

Nakamaye, K.L. et al., "Direct sequencing of polymerase chain reaction amplified DNA fragments through the incorporation of deoxynucleoside α–thiotriphosphates," Nucleic Acids Res., vol. 16, No. 21, pp. 9947–9959, 1988.

Ruffner, D. E. et al., "Thiophosphate interference experiments locate phosphates important for the hammerhead RNA self–cleavage reaction," Nucleic Acids Res., vol. 18, No. 20, pp. 6025–6029, 1990.

Almer, H. et al., "Nonenzymatic Hydrolysis of an RNA–dimer Containing a Thiophosphate Linkage," Nucleosides & Nucleotides, vol. 10, pp. 653–655, 1991.

Mag, M. et al., "Synthesis and selective cleavage of an oligodeoxynucleotide containing a bridged internucleotide 5'–phosphorothioate linkage," Nucleic Acids Res., vol. 19, No. 7, pp. 1437–1442, 1991.

Vyle, J.S. et al, "Sequence– and Strand–Specific Cleavage in Oligodeoxyribonucleotides and DNA Containing 3'–Thiothymidine," Biochemistry, vol. 31, pp. 3012–3018, 1992.

Podyminogin, M.A. et al., "Synthetic RNA–cleaving molecules mimicking ribonuclease A active center. Design and cleavage of tRNA transcripts," Nucleic Acids Res., vol. 21, No. 25, pp. 5950–5956, 1993.

Kuimelis, R.G. et al., "Cleavage properties of an oligonucleotide containing a bridged internucleotide 5'–phosphorothioate RNA linkage," Nucleic Acids Res., vol. 23, No. 23, pp. 4753–4760, 1995.

Wrzesinski, J. et al., "Specific RNA cleavages induced by manganese ions," FEBS Letters, vol. 374, pp. 62–68, 1995.

Moss, R.A. et al., "Remarkable acceleration of dimethyl phosphate hydrolysis by ceric cations," Chem. Commun., pp. 1871–1872, 1998.

Roelfes, G. et al., "Efficient DNA Cleavage with an Iron Complex without Added Reductant," J. Am. Chem. Soc., vol. 122, pp. 11517–11518, 2000.

Hodges, R.R. et al., "'Post–Assay' Covalent Labeling of Phosphorothioate–Containing Nucleic Acids with Multiple Fluorescent Markers," Biochemistry, vol. 28, pp. 261–267, 1989.

Fidanza, J.A. et al., "Introduction of Reporter Groups at Specific Sites in DNA Containing Phosphorothioate Diesters," J. Am. Chem. Soc., vol. 111, pp. 9117–9119, 1989.

Fidanza, J.A. et al., "Site–Specific Labeling of DNA Sequences Containing Phosphorothioate Diesters," J. Am. Chem. Soc., vol. 114, pp. 5509–5517, 1992.

Vlassov, V.V. et al., "Cleavage of tRNA with imidazole and spermine imidazole constructs: a new approach for probing RNA structures," Nucleic Acids Res., vol. 23, No. 16, pp. 3161–3167, 1995.

Ramsay, G., "DNA chips: State–of–the–art," Nature Biotechnol., vol. 16, pp. 40–44, 1998.

Ginot, F., "Oligonucleotide Micro–Arrays for Identification of Unknown Mutations: How Far from Reality?" Human Mutation, vol. 10, pp. 1–10, 1997.

Cheng, J. et al., "Microchip–based Devices for Molecular Diagnosis of Genetic Diseases," Molec. Diagnosis, vol. 1, No. 3, pp. 183–200, 1996.

Livache, T. et al., "Preparation of a DNA matrix via an electrochemically directed copolymerization of pyrrole and oligonucleotides bearing a pyrrole group," Nucleic Acids Res., vol. 22, No. 15, pp. 2915–2921, 1994.

Cheng, J. et al., "Preparation and hybridization analysis of DNA/RNA from *E. coli* on microfabricated bioelectronic chips," Nature Biotechnol., vol. 16, pp. 541–546, 1998.

Trawick, B.N. et al., "Inorganic Mimics of Ribonucleases and Ribozymes: From Random Cleavage to Sequence–Specific Chemistry to Catalytic Antisense Drugs," Chem. Rev., vol. 98, pp. 930–960, 1998.

Oivanen, M. et al., "Kinetics and Mechanisms for the Cleavage and Isomerization of the Phosphodiester Bonds of RNA by Bronsted Acids and Bases," Chem. Rev., vol. 98, pp. 961–990, 1998.

Longo, M.C. et al., "Use of uracil DNA glycosylase to control carry–over contamination in polymerase chain reactions," Gene, vol. 93, pp. 125–128, 1990.

Walker, G.T. et al., "Isothermal in vitro amplification of DNA by a restriction enzyme/DNA polymerase system," Proc. Natl. Acad. Sci. USA, vol. 89, pp. 392–396, 1992.

Bibillo, A. et al., "The non–enzymatic hydrolysis of oligoribonucleotides VI. The role of biogenic polyamines," Nucleic Acids Res., vol. 27, No. 19, pp. 3931–3937, 1999.

Sentagne, C. et al., "DNA cleavage photoinduced by new water–soluble zinc porphyrins linked to 9–methoxyellipticine," J. Photochem. Photobiol. B., vol. 16, pp. 47–59, 1992.

Nadji, S. et al., "Photochemically and Photoenzymatically Cleavable DNA," J. Am. Chem. Soc., vol. 114, pp. 9266–9269, 1992.

Povsic, T.J. et al., "Sequence–Specific Alkylation of Double–Helical DNA by Oligonucleotide–Directed Triple–Helix Formation," J. Am. Chem. Soc., vol. 112, pp. 9428–9430, 1990.

Kozal, M.J., "Extensive polymorphisms observed in HIV–1 clade B protease gene using high–density oligonucleotide arrays," Nature Med., vol. 2, No. 7, pp. 753–759, 1996.

* cited by examiner

US 6,489,114 B2

PROCESS FOR LABELING A RIBONUCLEIC ACID, AND LABELED RNA FRAGMENTS WHICH ARE OBTAINED THEREBY

This application claims the benefit of Provisional application Ser. No. 60/172,135, filed Dec. 17, 1999.

FIELD OF THE INVENTION

The present invention relates to a novel process for labeling a ribonucleic acid (RNA) with signal amplification.

BACKGROUND OF THE INVENTION

The state of the art shows that there are a large number of methods for labeling nucleotides, oligonucleotides or nucleic acids; oligonucleotides and nucleic acids will be referred to by the term polynucleotides. Polynucleotides can be labeled either during synthesis or by incorporating at least one labeled nucleotide.

A first method comprises in attaching the label to the base, whether the latter is a natural base or a modified base. A second method proposes attaching the label to the sugar, again whether the latter be a natural sugar or a modified sugar. A third method relates to attaching the label to the phosphate.

In fact, a person of skill in the art who is to label a nucleotide or a nucleotide analogue or a nucleic acid is inclined to attach the label to the base or to the sugar, which offers him more convenience and more options. This is, furthermore, what emerges from studying a large number of documents such as EP-A-0.329.198, EP-A-0.302.175, EP-A-0.097.373, EP-A-0.063.879, U.S. Pat. Nos. 5,449,767, 5,328,824, WO-A-93/16094, DE-A-3.910.151 and EP-A-0.567.841 in the case of the base or EP-A-0.286.898 in the case of the sugar. Each of these documents is hereby incorporated by reference for all purposes.

The technique of attaching the label to the phosphate is more complex especially because nucleic acids are water soluble and the reactivity of phosphate in this media is lower compared to that in organic solvents.

Even so, some documents have proposed techniques for labeling the phosphate. This applies, for example, to document EP-A-0.280.058, hereby incorporated by reference for all purposes, which describes labeling a nucleotide by attaching the label to the phosphate, with the latter being attached to the sugar in the 3' and/or 5' positions, when the nucleotide is a deoxyribonucleotide, and in the 2', 3' and/or 5' positions when the nucleotide is a ribonucleotide. This document also describes a polynucleotide or oligonucleotide which comprises at least one labeled nucleotide as described above; this nucleotide is incorporated into the polynucleotide or oligonucleotide during synthesis.

However, the labeling strategy which is proposed by document EP-A-0.280.058 does not enable the nucleic acids to be labeled uniformly. The incorporation of the labeled nucleotides into the polynucleotides cannot be controlled; it depends entirely on the composition of synthesized polynucleotides. Thus, some polynucleotides may contain a large number of labeled nucleotides whereas others may not contain any at all. As a result, the intensity of the signal emitted by these nucleic acids will not be uniform, and therefore it will be difficult to interpret the results when detecting the nucleic acids.

In this case, the labeling is incorporated biologically without any control of the positions of the labeled nucleotides.

The document U.S. Pat. No. 5,317,098 hereby incorporated by reference for all purposes relates to nucleic acids which are labeled at their 5' ends. This attachment uses imidazole and a linker arm. There is no associated fragmentation with the labeling. Furthermore, phosphate is added to nucleic acids and therefore kinase is used as a mean to introduce the phosphate, leading to at least one additional biological step. This document describes the labeling of a 15 mer oligonucleotide. When using large nucleic acids instead of oligonucleotide, this technique leads to the presence of a label only at the 5' end and the specific activity of the labeled nucleic acid is low.

In addition, when the labeling is carried out on large nucleic acids without a fragmentation stage, also termed a cleavage stage, the kinetics of hybridization of these labeled nucleic acids to their complementary sequences, is slow leading to poor hybridization yield. This will therefore result in a quantitative and qualitative loss of the signal. Steric hindrance is a key factor in this reaction.

Steric hindrance may not only be the result of the length of the nucleic acid but also of the existence of secondary structures. Fragmentation helps to broke (or reduce) these structures and in this way to optimize hybridization. Steric hindrance plays a particularly important role in the case of hybridization to solid surfaces which contain a high density of capture probes, for example the DNA arrays developed by the company Affymetrix, Inc. ("Accessing Genetic Information with High-Density DNA arrays", M. Chee et al., Science, 274, 610–614, 1996. "Light-generated oligonucleotide arrays for rapid DNA sequence analysis", A. Caviani Pease et al., Proc. Natl. Acad. Sci. USA, 91, 5022–5026, 1994, U.S. Pat. Nos. 5,744,305, 5,445,934). Each of these references is incorporated therein by reference for all purposes. In this technology, the capture probes are generally of reduced size, being of about twenty nucleotides in length.

A large number of methods are described in the state of the art for fragmenting nucleic acids.

First, the fragmentation can be enzymatic, i.e. the nucleic acids can be fragmented by nucleases (DNases or RNases) (Methods in Enzymol., vol. 152, S. Berger and A. Kimmel, ed. Academic Press, 1987, Enzymatic techniques and Recombinant DNA Technology, <Guide to Molecular cloning >, p91–110, Molecular Cloning, a Laboratory Manual, J. Sambrook, E. F. Fritsch and T. Maniatis, Cold Spring Harbor Laboratory Press, $2^{nd}$ Edition, p5.30–5.95, 1989). Each of these documents is hereby incorporated by reference for all purposes. Depending on the involved enzyme, this reaction generates small fragments or monomers having either a hydroxyl or a monophosphate group at their 5'-or 3'-ends.

Second, the fragmentation can be chemical. For example, in the case of DNA sequences, the depurination or depyrimidination using alkylating agents generates abasic sites which are then fragmented in the presence of a base by a mechanism termed "β-elimination" (T. Lindahl et al., Rate of Chain breakage at apurinic sites in double-stranded deoxyribonucleic acid., Biochemistry, 11, p3618–3623, 1972). The DNA's can be fragmented by oxidation, alkylation or free radical addition mechanisms, inter alia (M. Liuzzi et al., Characterization and damage in gamma-irradiated and OsO4-treated DNA using methoxyamine., Int. J. Radiat. Biol., 54, p709–722, 1988). Metal cations, which are often combined with organic molecules used as chemical catalysts, for example imidazole, are used for fragmenting RNA's. (R. Breslow and R. Xu, Recognition and catalysis in nucleic acid chemistry, Proc. Natl. Acad. Sci. USA, 90, p1201–1207, 1993. J. Hovinen et al. Imidazole Tethered oligonucleotides: Synthesis and R cleaving activity, J. Org. Chem., 60, p2205–2209, 1995). This fragmentation is preferably carried out in an alkaline medium and generates fragments having 3'-phosphate ends. Each of these documents is hereby incorporated by reference for all purposes.

However, the objective of these fragmentations is not that of facilitating or permitting labeling.

Document WO-A-88/04300 proposes a method for fragmenting and labeling RNA, using RNA molecules which possesses enzymatic properties, i.e. ribozymes. Cleavage catalysis with these ribozymes is sequence specific and the reaction yields to RNA fragments having a hydroxyl group (OH) at their 5' end and a monophosphate at 3' end. The labeling, which is solely radioactive labeling, is then effected by incorporating an added radioactive phosphate which is derived from a molecule of GTP. It is a phosphotransferase activity of these ribozymes category, i.e a kinase activity. The radioactive phosphate attachment is effected solely at the hydroxyl group at 5' end and no phosphate resulting from fragmentation is used for attaching the label to RNA fragments. Furthermore, the fragmentation is only carried out by ribozymes, implying the existence of a specificity between the ribozymes and the target nucleic acids to be cleaved. The phosphate then acts as the label.

Our invention allows the label attachment to the phosphate of a nucleic acid fragment which is released during the cleavage. There is no specificity and therefore, any type of nucleic acid can be fragmented in a random manner. The homogeneity of labeling intensity can be obtained using this approach since the labeling yield of each class of produced fragments is completely independent on its sequence and composition. Thus, our process makes it possible to prepare detection probes, for example. Finally, the phosphate is only a linker arm between the nucleic acid and the label.

The technique of signal amplification is well known in the field of immunoassays or nucleic acid probes as described for example in WO95/08000, or in the article J. Histochem. Cytochem. 45: 481–491, 1997 (each of which is incorporated by reference in its entirety for all purposes), but without fragmentation associated during the labeling.

No process of fragmenting before labeling with signal amplification has been described in the prior art.

The present invention therefore proposes a process which overcomes the previously mentioned drawbacks. Thus, this process makes it possible to obtain RNA fragments which are uniformly labeled once the fragmentation has been completed. In addition, the fragmentation makes it possible to obtain fragments which are of an optimum size for a possible hybridization. With the quality of the hybridization having been improved, the post-hybridization detection of labeled fragments will be more rapid and efficient. Finally, the invention improves the sensitivity by increasing the signal intensity produced and the ratio signal versus the background.

SUMMARY OF THIS INVENTION

To this end, the present invention relates to a process for labeling a synthetic or natural ribonucleic acid (RNA), characterized in that it comprises:
fragmenting the RNA,
fixing a first ligand to the terminal phosphate which is located at the 3' end and/or the 5' end of each fragment of said RNA, said terminal phosphate having been released during the fragmentation, and
binding a labeling agent to said first ligand.

DETAILED DESCRIPTION OF THE INVENTION

In the present invention, RNA (ribonucleic acid or polyribonucleic acid) is a synthetic or natural RNA.

Those of skill in the art will be familiar with methods of obtaining synthetic RNA. These methods include, for example, amplification techniques (see, for example, Kozal M. J. and al, Nature Medicine, 2(7), 753–758, 1996, hereby incorporated by reference in its entirety for all purposes), transcriptional amplification techniques or other methods leading to RNA products including TMA (Transcription Mediated Amplification), NASBA (Nucleic Acid Sequence-Based Amplification), 3SR (Self-Sustained Sequence Amplification), Qβ replicase amplification, natural RNA digestion by enzymes, and polyribonucleotide chemical synthesis (see, for example, U.S. Pat. Nos. 5,554,516 and 5,766,849 and Clin. Microbial. Rev.,5(4), p.370–386, 1992 each of which is incorporated by reference in its entirety for all purposes. Synthetic RNA is also RNA which comprises at least one modified nucleotide or at least one modified internucleotidic bond such as thiophosphate. A Natural RNA is a RNA which is obtained by extraction from a cell, for example a messenger RNA (mRNA), a ribosomal RNA (rRNA) or a transfer RNA (tRNA). Labeling is the attachment of a label which is able to generate a detectable signal. The following is a non-limiting list of these labels:

enzymes which produce a detectable signal, for example by colorimetry, fluorescence, luminescence, such as horseradish peroxidase, alkaline phosphatase, β-galactosidase and glucose-6-phosphate dehydrogenase, chromophores, such as fluorescent and luminescent compounds and dyes, groups having an electron density which can be detected by electron microscopy or by their electrical properties such as conductivity, amperometry, voltametry and impedance, detectable groups, for example whose molecules are of sizes which are sufficient to induce detectable modifications in their physical and/or chemical characteristics; this detection can be effected by means of optical methods such as diffraction, surface plasmon resonance, surface variation and angle of contact variation, or physical methods such as atomic force spectroscopy and the tunnel effect, radioactive molecules such as $^{32}P$, $^{35}S$ or $^{125}I$.

The compound which comprises the label is the labeling agent.

The term <fixing> means creating a covalent or a non covalent bond. An antibody selective of a phosphate or thiophosphate is a means to create a non covalent bond. According to a preferred mode of operation, the fixation is covalent as described in the examples.

In one aspect of the present invention, the fragmentation and the fixation are effected in one step.

In another aspect of the present invention, the fragmentation and the fixation are effected in two steps.

According to a first embodiment, the binding of the labeling agent to the first ligand is covalent. The different reactive functions which allows the covalent coupling are well known to those of skill in the art and some examples of conjugation could be found for example in <Bioconjugate techniques>, Hermanson G. T., Academic Press, San Diego, 1996. Hereby incorporated by reference in its entirety for all purposes.

According to a second embodiment, the binding of the labeling agent to the first ligand is non covalent. The non covalent binding is a binding involving, for examples, ionic or electrostatic interactions, Van der Vaals' interactions, hydrogen bonds or a combination of different interactions.

In a preferred embodiment, the binding of the labeling agent to said first ligand is effected indirectly. The first ligand, fixed to the terminal phosphate, is bound to a first antiligand, said first antiligand is bound to a second ligand and the labeling agent is a second antiligand bearing at least one label and able to react with said second ligand.

The (antiligand/ligand) combination means two compounds which are able to react together in a specific manner.

First ligand/first antiligand and second ligand/second antiligand combinations are selected, for example, from the group consisting of biotin/streptavidin, hapten/antibody, antigen/antibody, peptide/antibody, sugar/lectin and polynucleotide/complementary polynucleotide.

These different combinations and other combinations are known and described for example in BioMerieux applications WO 96/19729, WO 94/29723, WO 95/08000 which are incorporated herein by reference.

The first and second ligands are the same or different.

In a preferred mode of operation, the first ligand is a derivative of fluorescein and the second ligand is a derivative of biotin.

In another preferred mode of operation, the first ligand is a derivative of biotin and the first antiligand is a derivative of streptavidin.

There is no limitation in stacking-up other entities (ligand/antiligand) to increase signal amplification. For example, a (second ligand/first antiligand) entity binds to the first ligand fixed to the phosphate, then a (third ligand/second antiligand) entity binds to the second ligand and the labeling agent is a third antiligand bearing at least one label and able to react with the third ligand.

The addition of different entities may be effected in at least one step or each entity may be added successively after the fixation of the ligand to the phosphate.

According to a preferred mode of operation, the fixation of the first ligand to the 3' end of each fragment of the RNA is effected apart from the fragment which constitutes the 3' and/or 5' end of the starting RNA. Additionally or alternatively, the fixation of first ligand to the 5' end of each fragment of the RNA is effected apart from the fragment which constitutes the 5' end of the starting RNA.

Whatever the embodiment, fixation of the first ligand to the 3' end or the 5' end of an RNA fragment is effected by reacting a reactive function, which is carried out by the first ligand, to the phosphate which is in the 2' position, in the 3' position or in the cyclic monophosphate 2'-3' position, with respect to the ribose.

Fragmentation and/or the fixation of the first ligand to the 3' end or the 5' end of an RNA fragment is effected by binding a nucleophilic, electrophilic or halide function which is carried by a ligand to the phosphate in the 2' position, in the 3' position or in the cyclic monophosphate 2'-3' position, with respect to the ribose.

Fragmentation of the RNA is effected enzymatically, chemically or physically.

Enzymatic fragmentation of the RNA is carried out by nucleases.

Chemical fragmentation of the RNA is carried out by metal cations which may or may not be combined with a chemical catalyst.

In this case, the metal cations are $Mg^{++}$, $Mn^{++}$, $Cu^{++}$, $Co^{++}$ and/or $Zn^{++}$ ions and the chemical catalyst comprises imidazole, a substituted analogue, for example N-methylimidazole, or any chemical molecule which has an affinity for the RNA and which carries an imidazole ring or a substituted analogue.

Physical fragmentation of the RNA is carried out by sonication or by radiation.

In all the cases in point, the fixation of the first ligand to the 3' end or the 5' end of an RNA fragment is effected by reacting a molecule R-X, where R comprises the ligand and X is the reactive function, such as a hydroxyl, amine, hydrazine, alkoxylamine, alkyl halide, phenylmethyl halide, iodoacetamide or maleimide. X reacts to the phosphate which is linked to the 2' position, to the 3' position or to the cyclic monophosphate 2'-3' position of the ribose. In a preferred embodiment, X is an alkyl halide, phenylmethyl halide, iodoacetamide or maleimide. In order to facilitate the fixation of the ligand, a linker arm is optionally present between the ligand and the reactive function. In a preferred embodiment, R-X is N-(biotinoyl)-N'-(iodoacetyl) ethylenediamine, (+)-Biotinyl-iodoacetamidyl-3,6-dioxaoctanediamine, N-Iodoacetyl-N-biotinylhexylenediamine, 5-(bromomethyl) fluorescein.

The present invention also comprises a RNA fragment which is obtained by the above process,. The RNA fragment possesses at the 3' end or the 5' end a single nucleotide which is labeled at the terminal phosphate which was released during fragmentation.

This RNA fragment comprises from 10 to 150 nucleotides, preferably from 30 to 70 nucleotides and preferably from 40 to 60 nucleotides to facilitate hybridization of the RNA fragment to a probe or a target.

According to a preferred embodiment, the RNA fragment comprises at least one thiophosphate nucleotide.

In addition, the nucleotide bearing the ligand is a thiophosphate nucleotide.

According to a preferred embodiment the RNA fragment comprises at the 3' end a phosphate or a thiophosphate bearing a fluorescein bound to an anti-fluorescein antibody bearing at least one biotin, said antibody bound to a labeled streptavidin.

The invention relates to the use of an RNA fragment, as defined above, as a probe for detecting an RNA and/or a DNA or an RNA fragment and/or a DNA fragment.

The invention finally relates to the use of an RNA fragment, as defined above, as a labeled target which is able to bind to a capture probe.

Figure 1:
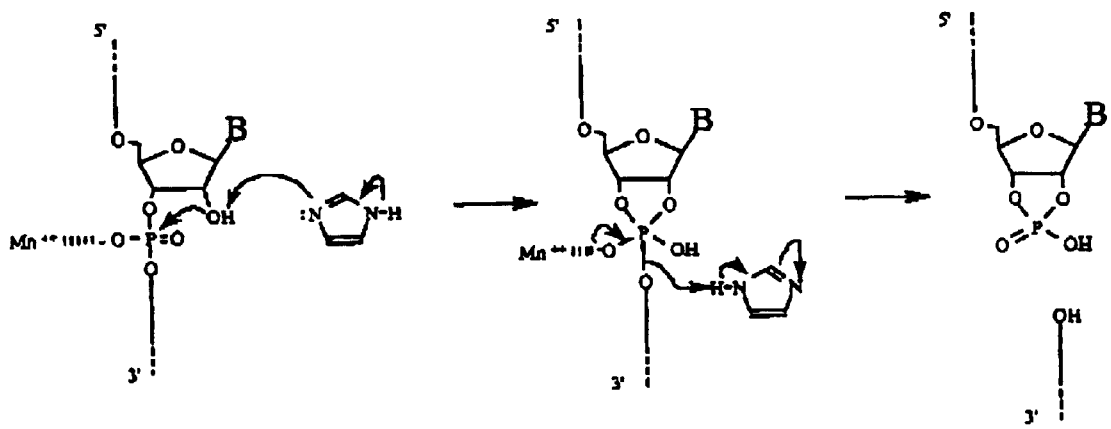
FIG. 1 shows a diagram of the chemical fragmentation of an RNA in the presence of $Mn^{++}$ cations and imidazole.
Figure 2:
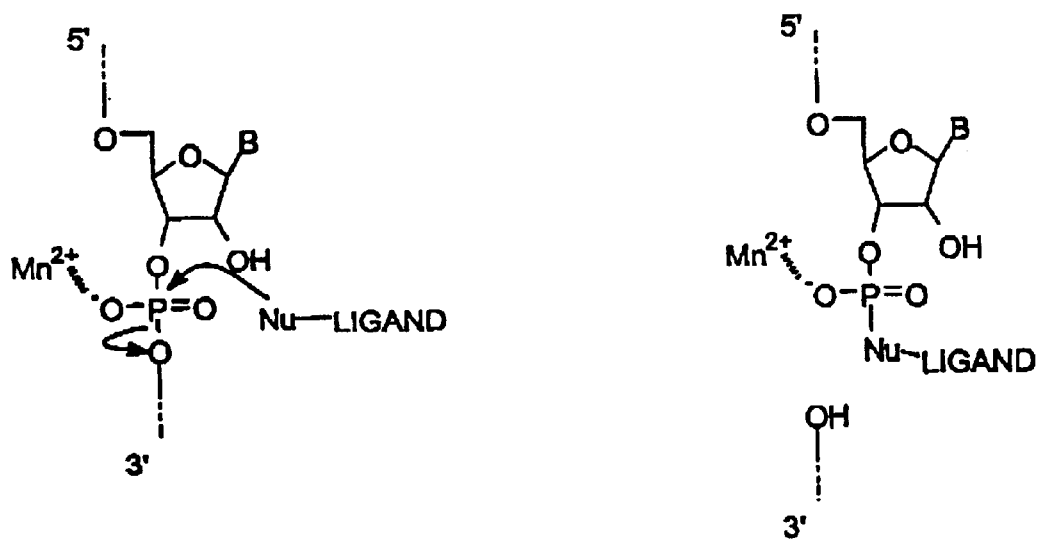
FIG. 2 shows a diagram of a possible mechanism of the fragmentation and labeling of an RNA with a ligand which carries a nucleophilic function.

Figures and examples represent particular embodiments and cannot be regarded as limiting the scope of the present invention.

EXAMPLE 1

Signal Amplification During LDC (Labeling During Cleavage) with RNA Amplicons 1.1 Preparation of Amplicons:

From isolates, one or two freshly grown colonies of bacteria (*Mycobacterium tuberculosis* (ATCC-27294) on Lowenstein-Jensen Medium; 3- to 5-mm diameter; ca. $10^8$ bacteria) were scraped on the end of a spatula and resuspended into 250 μl of sterile water in a 1.5 ml Eppendorf Tube. Total nucleic acids were released from culture material by vortexing the bacterial suspension in the presence of glass beads. A 5 µl aliquot of the lysate was added directly to the PCR. The 16 S hypervariable region was PCR amplified with Mycobacterium genus primers (positions 213 to 236 and 394 to 415 on the *M. tuberculosis* reference sequence M20940 [GenBank]; *M. tuberculosis* amplicon size is 202 bp.).

PCR was carried out in a 100-µl reaction volume containing 50 mM KCl, 10 mM Tris (pH 8.3), 1.5 mM $MgCl_2$, 0.001% (wt/vol) gelatin, 5% (vol/vol) dimethyl sulfoxide, 0.5 µM (each) primer, 200 'µM (each) deoxynucleotides triphosphates, and 1.5 U of Taq polymerase (AmpliTaq; Perkin-Elmer, Norwalk, Conn.). PCR was performed in a Perkin Elmer 2400 thermal cycler with an initial denaturation step at 94° C. for 5 min and cycling conditions of 94° C. for 45 s, 60° C. for 30 s and 72° C. for 30 s for 35 cycles and 72° C. for 10 min for the last cycle. PCR product were analyzed by agarose gel electrophoreris.

Promoters-tagged PCR amplicons were used for generating labeled single-stranded RNA targets by in vitro transcription. Each 20-µl reaction mixture contained approximately 50 ng of PCR product; 20 U of T3 or T7 RNA polymerase (Promega); 40 mM tris acetate (pH 8.1) ; 100 mM $Mg(acetate)_2$; 10 mM dithiothreitol; 1.25 mM ribonucleotides triphosphates (ATP, CTP, GTP, and UTP). The reaction was carried out at 37° C. for 1 h.

1.2 Labeling during cleavage of amplicons:

RNA amplicons were prepared as described in 1.1. To RNA molecules (1 µl of reaction mixture), 6 µl Imidazole (0.1M in pure water), 6 µl of $MnCl_2$ (1M in pure water) and 2 µl of 5-(bromomethyl)fluorescein (5-BMF provided by Molecular Probes, Eugene, Oreg., USA, under reference B1355; 100 mM in DMSO) and pure water were added for a final volume of 100 µl. Reactional medium was homogenized and incubated at 65° C. during 30 min.

1.3 Protocol for DNA-arrays analysis:

The DNA chip used for analysis of Mycobacteria amplicons is the same as described by A. Troesch et al in J. Clin. Microbiol., 37(1), p 49–55, 1999. Hereby incorporated by reference in its entirety for all purposes. The analysis was performed on the GeneChip® instrument system (reference 900228, Affymetrix, Santa Clara, Calif.) which comprises the GeneArray® scanner, the GeneChip® hybrization oven, the GeneChip® fluidics station and the GeneChip® analysis software.

1.4 Antibody staining:

The first step of hybridization, was performed on DNA-arrays using the protocol described in the article incorporated by reference above. The array was then flushed and a second step of staining was performed using staining solution containing 300 µl of MES (reference Aldrich 16373-2, 2 M in pure water), 2.4 µl of Acetylated Bovine Serum Albumin, 6 µl of Normal Goat IgG, 1.2 µl of Anti-fluorescein antibody, and pure water for a final volume of 600 µl.

Anti-fluorescein, rabbit IgG fraction, biotin-XX conjugate (Ab-antiFbiot), was supplied by Molecular Probes (Eugene, Oreg. reference A-982)

Acetylated Bovine Serum Albumin (acetylated BSA) solution was supplied by GibcoBRL Life Technologies, (Rockville, Md. reference 15561-020)

Goat IgGReagent Grade was supplied by Sigma chemical, (St. Louis, Mo. reference I-5256)

After 10 minutes of hybridization, the array was flushed, washed with a washing buffer containing 6 X SSPE-Tween 0.01%, and a third step of hybridization was performed, using second staining solution defined as: 300 µl of MES (2 M in pure Water), 6 µl of acetylated BSA and 6 µl of Streptavidin, R-Phycoerythrin conjugate, and pure water for a final volume of 600 µl.

Streptavidin, R-Phycoerythrin conjugate (SRPhy), was supplied by Molecular Probes (Eugene, Oreg. Reference S-866)

After 10 minutes of hybridization, the array was flushed and washed using same washing buffer as defined in the second step.

The results in terms of nucleotide base call percentage (BC %), mean signal intensities for probe arrays cells (S expressed in Relative Fluorescence Unit RFU), mean background intensities (B expressed in RFU) and the ratio S/B are generated by functions available on GeneChip® software and are reported in the table below.

| Description | BC % | S | B | S/B |
| --- | --- | --- | --- | --- |
| Direct labeling with 5-BMF | 91.4 | 9095 | 4179 | 2.2 |
| Antibody staining | 99.5 | 17884 | 2049 | 8.7 |

The data above showed that the signal amplification using antibody staining improves base call percentage and intensity level. The ratio signal versus the background is also improved.

EXAMPLE 2

Antibody Staining of Synthesized Oligodeoxyribonugleotides as a Medal for Labeling 2.1. Preparation of oligonucleotide 3'-monothiophosphate.

Oligoribonucleotide (ODN-ps) (5'-CUG AAC GGU AGC AUC UUG AC-3') bearing a monophosphate group at the 3'-end was prepared by Eurogentec (Seraing Belgium) using the phosphoramidite chemistry.

2.2. Labeling during cleavage of oligonucleotide.

Oligoribonucleotide 3'-monothiophosphate was prepared as described in 2.1.

To this oligonucleotide (5 µl, 1 nmol) 3 µl Imidazole (0.1M in pure water), 3 µl of $MnCl_2$ (1M in pure water) and 2 µl of one of four labels (100 mM) and pure water were added for a final volume of 50 µl. Reaction medium was homogenized and incubated at 65° C. for 30 min.

Different labels were tested:

Label a: N-(biotinoyl)-N'-(iodoacetyl)ethylenediamine (100 mM in DMSO) (Molecular Probe reference B-1591)

Label b: (+)-Biotinyl-iodoacetamidyl-3,6-dioxaoctane diamine (100 mM in pure water) (pierce, Rockford, Ill., reference 21334) iodoacetyl-PEO-biotin.

Label c: N-Iodoacetyl-N-biotinylhexylenediamine (100 mM in DMF) (Pierce, Rockford, Ill., reference 21333)

Label d: 5-(bromomethyl)fluorescein (100 mM in DMSO) a control of the detection without signal amplification.

2.3 Hybridization

500 µl of hybridization buffer (1.5 ml 20X SSPE+250 µl Triton1%+3.250 ml pure water (6X SSPE 0.05% triton) was then added and this solution was vortexed. The reaction product was hybridized as described in example 1.

2.4 Antibody staining:

Another step of hybridization was performed on a DNA-checkerboard as described in example 1.4 for the 3 labeling agents bearing a biotin. For label d, analysis was performed directly without the additional step of antibody staining.

This step of staining was performed using staining solution containing 300 µl of MES (2 M in pure Water), 60 µl of acetylated BSA, 6 µl of Streptavidin, R-Phycoerythrin conjugate (SRPhy), and pure water for a final volume of 600 µl. Acetylated Bovine Serum Albumin (BSA) solution was supplied by GibcoBRL Life Technologies, (Rockville, Md. Reference 15561-020). Streptavidin, R-Phycoerythrin conjugate, was supplied by Molecular Probes (Eugene, Oreg. Reference S-866)

After 10 minutes of hybridization, the array was flushed and washed using washing buffer 6 X SSPE-Tween 0.01%.

Detection and analysis were performed on DNA-checkerboard array as described in example 1.

This DNA-checkerboard array is designed to analyze the sequence complementary to ODN-ps by a 4-tiling approach as described in WO 9511995.

Analysis:

The results in terms of base call percentage (BC %) intensity levels (S), background (B) and the ratio S/B are reported in the table below:

| Label used | BC % | S | B | S/B |
|---|---|---|---|---|
| d | 92.5 | 7049 | 2240 | 3.2 |
| a | 100 | 41961 | 1811 | 23.2 |
| b | 100 | 31301 | 1510 | 20.7 |
| c | 100 | 44457 | 2219 | 20.0 |

The signal amplification using a biotin derivative and antibody staining instead of direct labeling with 5-(bromomethyl) fluorescein in the LDC is better in terms of base call percentage and intensity level.

EXAMPLE 3

Signal Amplification During LDC (Labeling During Cleavage) with Natural RNA 3.1. RNA Isolation Total RNA was isolated from *Escherichia coli* strain MG1655 grown in LB broth (Teknova). The cells were grown to mid-log phase at 37° C. and harvested by centrifugation. RNA was isolated using the RNeasy kit (Qiagen). The isolated RNA was quantitated by absorbance measurements taken at 260 nm. 3.2. RNA Fragmentation and labeling:

RNA was labeled with fluorescein by combining the following in a final volume of 100 µl: 8 µg of RNA, 30 mM CHES (Aldrich, reference 22403-0), pH 9–9.5, 1 mM 5-(bromomethyl)fluorescein (Molecular Probes, added from a 50 mM stock in dimethylformamide), 30 mM manganese chloride. The components were placed in a PCR tube, heated to 65° C. for 40 min and cooled to 4° C. in a GeneAmp PCR System 2400 Instrument (Perkin Elmer). To label the RNA with biotin the following were combined in a final volume of 100 µl: 10 µg of RNA, 30 mM MOPS (Aldrich reference 16377-5), pH 7.5, 20 mM PEO-iodoacetyl- -biotin (Pierce Rockford, Ill., ref: 21334), 10 mM magnesium chloride. The components were placed in a PCR tube, heated to 95° C. for 30 min, then 25° C. for 30 min and cooled to 4° C. in a PCR instrument as above. Labeled RNA fragments were precipitated after the addition of 25 µg of carrier glycogen. Control RNA spikes (2 fentomoles each) were added to the *E. coli* RNA prior to labeling. The control RNA spikes were produced by in vitro transcription of linearized plasmid templates.

3.3.Probe array hybridization and signal amplification.

Hybridizations were performed on an *E. coli* Sense probe array (Affymetrix). The probe array is based on the sequence of *E. coli* K-12 ("The complete genome sequence of *Escherichia coli* K-12", Blattner, F. et al., Science, 277, 1453–1474, 1997, hereby incorporated by reference in its entirety for all purposes). The array contains 15 probe pairs for every RNA or protein-encoding region designated by a b# (Blattner et al., ibid.). For these regions, the probe sets are complementary to the native RNA (sense strand). The array also contains probe sets to regions located between the b# regions. These are called intergenic regions. In this case, the probe set represents both orientations of the intergenic regions. In addition the probe array contains probe sets to a number of control sequences. Many of these controls may be spiked into the sample and serve as positive hybridization controls. The cell feature size of the array is (23.5×23.5) µm², and the synthesis area is (12.8×12.8) mm².

The hybridization solution contained 10 µg of fluorescein-labeled RNA fragments or 5 µg of biotin-labeled RNA fragments in a final volume of 200 µl containing 100 mM MES, pH 6.5–7.0, 1 M, Nat 20 mM EDTA, 0.01% (v/v) Tween 20, 0.5 nM control oligonucleotide (fluorescein or biotin labeled, matching the RNA sample), 0.1 mg/mL sheared and denatured herring sperm DNA and 0.5 mg/ml acetylated BSA. The hybridization solution was injected directly into the probe array cartridge and hybridized in a GeneChip® Hybridization Oven (Affymetrix, Santa Clara, Calif.) at 45° C. for 16 hr. Washes and stains were done on the GeneChip® Fluidics Station (Affymetrix). The wash solutions were defined as follows: Stringent Wash Buffer, 100 mM MES, pH 6.5–7.0, 0.1 M Na⁺, 0.01% (v/v) Tween 20; Non-Stringent Wash Buffer, 6X SSPE (from 20X stock, BioWhittaker), 0.01% (v/v) Tween 20, 0.005% (v/v) Antifoam 0–30 (Sigma). For the fluorescein labeled RNA hybridizations, the probe arrays were placed on the Fluidics Station and washed with Von-Stringent Wash Buffer (10 cycles of 2 mixes/cycle at 25° C.), followed by Stringent Wash Buffer (4 cycles of 15 mixes/cycle at 50° C.) and filled with Non-Stringent Wash Buffer prior to scanning. Fluorescein-labeled probe arrays were scanned on the Gene-Array® Scanner (Hewlett Packard) using the following scan parameters: 3 µm pixel, 530 nm wavelength. Following the scan, the fluorescein signal was amplified by mixing the array with 600 µL of 2 µg/mL anti-fluorescein antibody, biotin conjugate (Ab-antiFbiot), 0.1 mg/ml normal goat IgG, and 2 mg/ml acetylated BSA in 100 mM MES, pH 6.5–7.0, 1 M Na⁺, 0.05% (v/v) Tween 20 and 0.005% (v/v) Antifoam 0–30 for 10 min at 25° C. The antibody binding was followed by staining the array with 600 µL of 10 µg/mL streptavidin, R-phycoerythrin (SRPhy) in 100 mM MES, pH 6.5–7.0, 1 M Na⁺, 0.05% (v/v) Tween 20, 0.005% (v/v) Antifoam 0–30 and 5 mg/ml acetylated BSA for 10 min at 25° C. Following the streptavidin phycoerythrin stain, the array was washed with Non-Stringent Hybridization Buffer (10 cycles of 4 mixes/cycle at 30° C.). The array was scanned using the 3 µm pixel and 570 µm wavelength parameters. For biotin-labeled RNA hybridizations the probe arrays were washed with Non-Stringent Wash Buffer (10 cycles of 2 mixes/cycle at 25° C.), followed by Stringent Wash Buffer (4 cycles of 15 mixes/cycle at 50° C.) as described above. The array was then stained with streptavidin phycoerythrin as described above followed by a wash with Non-Stringent Wash Buffer (10 cycles of 4 mixes/cycle at 25° C.). The signal on the array was then amplified by mixing the array with 600 µL of 3 µg/ml anti-streptavidin antibody (goat), biotinylated (Vector Laboratories), 0.1 mg/ml normal goat IgG, and 2 mg/ml acetylated BSA in 100 mM MES, pH 6.5–7.0, 1 M Na⁻, 0.05% (v/v) Tween 20 and 0.005% (v/v) Antifoam 0–30 for 10 min at 25° C. The array was stained again with streptavidin phycoerythrin as described above followed by a wash with Non-Stringent Wash Buffer (15 cycles of 4 mixes/cycle at 30° C.). All of the steps were handled sequentially on the GeneChip® Fluidics Station. The array was then scanned using the 3 $\mu$m pixel and 570 nm wavelength parameters.

3.4. Data analysis:

The scan data was analyzed by GeneChip® Software (version 3.1, Affymetrix). Data was produced by using the Expression Analysis Algorithm set at default parameters. The present calls were selected from the coding sequences (stable RNA's and open reading frames) on the array. The Average Difference was defined as the intensity difference between the perfect match probe and the mismatch probe averaged over the 16 probe pairs used to define a coding sequence.

3.5. Results:

The results of the hybridizations are summarized in the following two tables.

TABLE 1

Total *E. coli* RNA Comparison

| | Fluorescein Label | | Biotin Label |
|---|---|---|---|
| | No Amplification | | Antibody Amplification |
| Present Calls | 826 | 1199 | 737 |
| % Present Calls | 19% | 28% | 17% |
| Total Coding Sequences | 4331 | 4331 | 4331 |
| Mean Avg. Difference | 6 | 180 | 147 |

Table 1 summarizes the results obtained from the coding sequences on the array. The value of the antibody amplification on fluorescein labeled target is clearly seen by comparing the number of present calls and the mean average difference values. In this case the additional signal generated by the antibody amplification increased the number of present calls from 826 to 1199 and increased the mean average difference from 6 to 180. The antibody amplification of biotin-labeled RNA produced mean average difference signals that are similar but slightly lower than those obtained with amplification of the fluorescein label. It should be noted the biotin-labeled sample was one-half the amount of the fluorescein-labeled sample.

TABLE 2

Control RNA Spike Comparison

| | Fluorescein Label | | | | Biotin Label | |
|---|---|---|---|---|---|---|
| | No Amplification | | Antibody Amplification | | | |
| Probe Set | Avg Diff[1]. | Abs. Call[2] | Avg Diff[1]. | Abs. Call[2] | Avg Diff[1]. | Abs. Call[2] |
| DapX-5 | 11 | P | 192 | P | 1237 | P |
| DapX-M | 0 | A | 111 | P | 507 | P |
| DapX-3 | 7 | P | 218 | P | 1554 | P |
| LysX-5 | 12 | P | 417 | P | 1795 | P |
| LysX-M | 3 | A | 150 | P | 702 | P |

TABLE 2-continued

Control RNA Spike Comparison

| | Fluorescein Label | | | | Biotin Label | |
|---|---|---|---|---|---|---|
| | No Amplification | | Antibody Amplification | | | |
| Probe Set | Avg Diff[1]. | Abs. Call[2] | Avg Diff[1]. | Abs. Call[2] | Avg Diff[1]. | Abs. Call[2] |
| LysX-3 | 3 | P | 154 | P | 384 | P |
| PheX-5 | 8 | P | 340 | P | 197 | P |
| PheX-M | 6 | P | 162 | P | 297 | P |
| PheX-3 | 5 | A | 358 | P | 1474 | P |
| ThrX-5 | 10 | P | 234 | P | 123 | P |
| ThrX-M | 9 | P | 144 | P | 196 | P |
| ThrX-3 | 6 | M | 233 | P | 337 | P |

[1]Average Difference
[2]Absolute Call, P = Present, A = Absent, M = Marginal

Table 2 summarizes data obtained with RNA control spikes. With the fluorescein-labeled spikes the antibody signal amplification greatly improved the mean average difference values converting any absent or marginal call into a present call. The biotin-labeled RNA spikes produced higher signals in 10 out of 12 probe sets when compared to the fluorescein-labeled spikes after antibody signal amplification.

What is claimed is:

1. A process for labeling with signal amplification a ribonucleic acid (RNA), comprising:
    fragmenting the RNA to form RNA fragments,
    fixing a first ligand to a terminal phosphate located at least one of the 3' end and the 5' end of each of a plurality of said RNA fragments, said terminal phosphate having been released during the fragmentation, and
    binding a plurality of labeling agents to said first ligand on each of a plurality of said fragments.

2. A process according to claim 1, wherein the binding of the labeling agents to said first ligand is effected indirectly.

3. A process according to claim 2, wherein a first antiligand is bound to said first ligand, a second ligand is bound to said first antiligand, and the labeling agent comprises a second antiligand bearing at least one label and able to react with said second ligand.

4. A process according to claim 3, wherein first ligand/first antiligand and second ligand/second antiligand combinations are selected from the group consisting of biotin/streptavidin, hapten/antibody, antigen/antibody, peptide/antibody, sugar/lectin and polynucleotide/complementary polynucleotide.

5. A process according to claim 4, wherein the first and second ligands are the same.

6. A process according to claim 4, wherein the first and second ligands are different.

7. A process according to claim 6, wherein the first ligand is a derivative of fluorescein and the second ligand is a derivative of biotin.

8. A process according to claim 1, wherein the first ligand is a derivative of biotin and the labeling agent is a derivative of streptavidin.

9. A process according to claim 1, wherein the fragmenting and the fixing are effected in one step.

10. A process according to claim 1, wherein the fragmenting and the fixing are effected in two steps.

11. A process according to claim 1, wherein the binding of the labeling agent to the first ligand is covalent.

12. A process according to claim 1, wherein the binding of the labeling agent to the first ligand is non-covalent.

13. A process according to claim 1, wherein the fixing is effected by reacting a reactive function, which is carried by said first ligand, to a phosphate which is in the 2' position, in the 3' position or in the cyclic monophosphate 2'–3' position, with respect to a ribose at the 3' end or the 5' end of the RNA fragment.

14. A process according to claim 1, wherein at least one of the fragmenting and the fixing is effected by reacting a nucleophilic, electrophilic or halide function which is carried by said first ligand to a phosphate in the 2' position, in the 3' position or in the cyclic monophosphate 2'–3' position, with respect to a ribose at the 3' end or the 5' end of the RNA fragment.

15. A process according to claim 1, wherein the fragmenting is effected enzymatically, chemically or physically.

16. A process according to claim 15, wherein the fragmenting is carried out enzymatically with at least one nuclease.

17. A process according to claim 15, wherein the fragmenting is carried out chemically with metal cations optionally combined with a chemical catalyst.

18. A process according to claim 1, wherein the fragmenting is carried out with metal cations selected from the group consisting of $Mg^{++}$, $Mn^{++}$, $Cu^{++}$, $Co^{++}$ and $Zn^{++}$ ions, and a chemical catalyst comprised of imidazole, a substituted imidazole analogue, or any chemical molecule which has an affinity for the RNA and which carries an imidazole nucleus or a substituted imidazole analogue.

19. A process according to claim 15, wherein the fragmenting is carried out physically by sonication or irradiation.

20. A process according to claim 1, wherein the fixing is effected by reacting a molecule R-X to a phosphate which is linked to the 2' position, to the 3' position or to the cyclic monophosphate 2'–3' position of a ribose at the 3' end or the 5' end of the RNA fragment, where R is the first ligand and X is a reactive function selected from the group consisting of hydroxyl, amine, hydrazine, alkoxylamine, alkyl halide, phenylmethyl halide, iodoacetamide and maleimide.

21. A process according to claim 20, wherein R-X is selected from the group consisting of 5-(bromofluorescein) and derivatives of iodoacetyl biotin.

22. A method of detecting at least one member selected from the group consisting of an RNA, a DNA, an RNA fragment and a DNA fragment, comprising probing a sample suspected of containing said member with a labeled RNA fragment- obtained by the process of claim 1, wherein the RNA fragment comprises at the 3' end or the 5' end a single nucleotide which is labeled at the terminal phosphate released during the fragmentation.

23. A method of detecting at least one member selected from the group consisting of an RNA, a DNA, an RNA fragment and a DNA fragment, comprising probing a sample suspected of containing said member with a labeled RNA fragment-, the RNA fragment comprising at 3' end a phosphate or a thiophosphate bearing a fluorescein bound to an anti-fluorescein antibody bearing at least one biotin, said antibody bound to a labeled streptavidin.

24. A method of binding a labeled target to a capture probe, comprising exposing said labeled target to said capture probe, wherein said labeled target is a labeled RNA fragment obtained by the process of claim 1, wherein the RNA fragment comprises at the 3' end or the 5' end a single nucleotide which is labeled at the terminal phosphate released during the fragmentation.

25. A method of binding a labeled target to a capture probe, comprising exposing said labeled target to said capture probe, wherein said labeled target is a labeled RNA fragment, the RNA fragment comprising at 3' end a phosphate or a thiophosphate bearing a fluorescein bound to an anti-fluorescein antibody bearing at least one biotin, said antibody bound to a labeled streptavidin.

* * * * *